(12) United States Patent
Schmidt

(10) Patent No.: US 8,734,316 B2
(45) Date of Patent: May 27, 2014

(54) BIOMOLECULAR WEARABLE APPARATUS

(75) Inventor: David Schmidt, Buford, GA (US)

(73) Assignee: LifeWave, Inc., San Diego, CA (US)

( * ) Notice: Subject to any disclaimer, the term of this patent is extended or adjusted under 35 U.S.C. 154(b) by 0 days.

(21) Appl. No.: 12/915,419

(22) Filed: Oct. 29, 2010

(65) Prior Publication Data

US 2011/0184356 A1   Jul. 28, 2011

Related U.S. Application Data

(63) Continuation of application No. 10/669,596, filed on Sep. 25, 2003, now abandoned.

(60) Provisional application No. 60/413,617, filed on Sep. 25, 2002.

(51) Int. Cl.
*A61N 1/00* (2006.01)
*A61N 2/00* (2006.01)
*A61N 1/30* (2006.01)

(52) U.S. Cl.
USPC .................... 600/15; 600/10; 600/13; 604/20

(58) Field of Classification Search
None
See application file for complete search history.

(56) References Cited

U.S. PATENT DOCUMENTS

| | | | |
|---|---|---|---|
| 3,658,070 A | 4/1972 | Diluzio | 131/267 |
| 4,746,508 A | 5/1988 | Carey et al. | 424/88 |
| 5,204,114 A | 4/1993 | Demopoulos et al. | 424/465 |
| 5,389,657 A | 2/1995 | Madsen | 514/369 |
| 5,393,350 A | 2/1995 | Schroeder | |
| 5,597,976 A | 1/1997 | Schroeder | |
| 5,618,823 A | 4/1997 | Cavalletti et al. | 514/283 |
| 5,651,973 A | 7/1997 | Moo-Young et al. | |
| 5,837,281 A | 11/1998 | Iga et al. | 424/449 |
| 5,860,428 A | 1/1999 | Lesser et al. | 131/331 |
| 5,939,094 A | 8/1999 | Durif et al. | 424/448 |
| 6,030,950 A | 2/2000 | Ohlenschlager | 514/18 |
| 6,475,514 B1 | 11/2002 | Blitzer et al. | |
| 6,558,695 B2 | 5/2003 | Luo et al. | |
| 6,617,306 B2 | 9/2003 | Stein et al. | 514/2 |
| 6,890,533 B2 | 5/2005 | Bomshteyn et al. | 424/179.1 |

(Continued)

FOREIGN PATENT DOCUMENTS

EP   0 616 803 A2   9/1994

OTHER PUBLICATIONS

Paramas et al., HPLC-fluorimetric method for analysis of amino acid in products of hive (honey and bee-pollen), Food Chemistry 95, (2006) 148-156.*

(Continued)

*Primary Examiner* — Isis Ghali
(74) *Attorney, Agent, or Firm* — Pillsbury Winthrop Shaw Pittman LLP

(57) ABSTRACT

This invention relates to an apparatus that regulates thermodynamic energy-flow within a human body for producing beneficial effects such as, for example, improvement in strength, improvement in stamina, pain relief, etc. According to one embodiment, the invention provides a wearable apparatus that may include biomolecular components for building-up of a thermomagnetic energy within the human body. According to another embodiment, the invention provides a wearable apparatus that may include biomolecular components for dilution of a thermomagnetic energy within the human body. According to yet another embodiment, the invention provides a wearable apparatus that may include biomolecular components having orthomolecular and/or non-orthomolecular organic materials which are capable of thermomagnetic levororotary action and/or thermomagnetic dextrorotatory action.

11 Claims, 5 Drawing Sheets

(56) References Cited

U.S. PATENT DOCUMENTS

| | | | |
|---|---|---|---|
| 6,896,899 B2 | 5/2005 | Demopolos et al. | 424/451 |
| 2002/0061870 A1 | 5/2002 | Pearson et al. | 514/184 |
| 2002/0072501 A1 | 6/2002 | Cyr et al. | |
| 2002/0156340 A1* | 10/2002 | Blendermann | 600/15 |
| 2003/0055103 A1 | 3/2003 | Heinzen et al. | 514/456 |
| 2003/0118615 A1 | 6/2003 | Blendermann | |
| 2003/0147812 A1 | 8/2003 | Ueberle | 424/9.52 |
| 2004/0057983 A1 | 3/2004 | Schmidt | 424/443 |
| 2005/0032708 A1 | 2/2005 | Bush et al. | 514/18 |
| 2005/0059153 A1 | 3/2005 | George et al. | 435/446 |
| 2005/0215871 A1 | 9/2005 | Feldman et al. | 600/309 |
| 2005/0271726 A1 | 12/2005 | Crum | 424/486 |
| 2006/0099244 A1 | 5/2006 | Guilford | 424/450 |
| 2006/0110474 A1 | 5/2006 | Asami | 424/757 |
| 2006/0208383 A1 | 9/2006 | Aisenbrey | 264/104 |
| 2007/0077258 A1 | 4/2007 | Guilford | 424/209.1 |
| 2008/0208179 A1 | 8/2008 | Chan et al. | 606/9 |
| 2008/0220092 A1 | 9/2008 | Dipierro et al. | 424/649 |
| 2010/0099762 A1 | 4/2010 | Bush et al. | 514/546 |
| 2010/0117029 A1 | 5/2010 | Ying | 252/301.36 |
| 2012/0165596 A1 | 6/2012 | Schmidt | 600/15 |

OTHER PUBLICATIONS

Negrao et al., "Carnitine supplementation and depletion: tissue carnitines and enzymes in fatty acid oxidation", The American Physiological Society, 1987.*

Miscellaneous Incoming Letter by Edward Blendermann, dated Jan. 9, 2013, and received by the U.S. Patent and Trademark Office on Jan. 14, 2013.

Objections to David Schmidt's Declaration by Edward Blendermann, dated Dec. 29, 2012, and received by the U.S. Patent and Trademark Office on Jan. 14, 2013.

U.S. Appl. No. 10/302,527, filed Jun. 23, 2006, Blendermann.

U.S. Appl. No. 60/074,248, filed Feb. 10, 1998, Blendermann.

Albert Roy Davis and Walter C. Rawis, "Magnetism and Its Effect on the Living System", Apr. 1996, Acres USA Publications.

Kao, Mu-Jung, et al., "Effects of Infrared and Low-Power Laser Irradiation on Cell Viability, Glutathione and Glutathione-Related Enzyme Activities in Primary Rat Hepatocytes", *Journal of Formos Med. Assoc.*, vol. 102, No. 7, Jul. 2003, pp. 486-491.

Kawakita, Yasunori., et al., "Increase of Intracellular Glutathione by Low-Dose Gamma-Ray Irradiation is Mediated by Transcription Factor AP-1 in RAW 264.7 Cells", *Biol Pharm Bull*, vol. 26, No. 1, Jan. 26, 2003, pp. 19-23.

Schaffer, M., et al., "Magnetic Resonance Imaging (MRI) Controlled Outcome of Side Effects Caused by Ionizing Radiation, Treated with 780 nm-Diode Laser—Preliminary Results", *Journal of Photochemistry and Photobiology B: Biology*, vol. 59 (1-3), Dec. 2000, pp. 1-8.

Ball, Louise, et al., "Evidence for a Direct Link Between Glutathione Biosynthesis and Stress Defense Gene Expression in *Arabidopsis*", *The Plant Cell*, vol. 16, Sep. 2004, pp. 2448-2462.

Hamblin, Michael R., et al., "Mechanisms for Low Level Light Therapy", *Proc. of SPIE*, vol. 6140, 614001, 2006, pp. 1-12.

* cited by examiner

BIOMOLECULAR WEARABLE APPARATUS

CROSS-REFERENCE TO RELATED APPLICATIONS

This application claims priority as a continuation of U.S. patent application Ser. No. 10/669,596, filed on Sep. 25, 2003, now abandoned, and incorporated herein by reference in its entirety, which claims priority from U.S. provisional patent application Ser. No. 60/413,617, filed Sep. 25, 2002, which is incorporated by reference herein in its entirety.

FIELD OF THE INVENTION

This invention relates generally to a biomolecular wearable apparatus regulating energy-flow, and more particularly to a biomolecular wearable apparatus regulating thermomagnetic energy flow within human body for producing beneficial effects including an improvement in stamina and a relief from a pain.

BACKGROUND OF THE INVENTION

Jewelries including ring, necklace, bracelets, and pendants are typically used for decorative purpose. However, there is a segment of the jewelry market that concerns itself for a purpose other than decorative. Examples of jewelries that are designed for the purpose other than decorative include copper bracelets and magnetic jewelries.

Copper bracelet is believed to perform functions of relieving pain and helping to alleviate symptoms of arthritis for a user. A mode of operation for these functions has been proposed as mobility of copper ions from the copper bracelet through the user's skin and into the user's blood stream. If the mobility of copper ions is the mode of operation of a copper bracelet, then an individual or a user could not obtain immediate relief from pain, etc., due to a long period of time required for this mode of operation to become effective. Accordingly, a drawback of existing systems with respect to a copper bracelet is that the therapeutic response—if any—takes place over a relatively long period of time. Another drawback of the existing systems is that the copper bracelets have a limited and narrow field of use.

Various types of magnetic jewelries are believed to perform functions of relieving pain and improving circulation. Clinical studies performed with magnetic jewelries indicated that there is an effect going on other than a placebo effect. An effect of a magnet on a human body could be due, in part, to the fact that human blood contains iron. In one theory, the iron in the blood causes the blood to be attracted to a part of the body in which the magnet is worn, resulting in improvement in circulation. However, there are biophysicists who question the efficacy of a magnetic jewelry. For example, it is well known that the DNA contains Hydrogen bonds. Because a magnet is polar in nature, a back emf from the magnet to the Hydrogen bonds may be possible. This might cause the Hydrogen to spin in opposition to what is normal and disassemble the DNA of that cell. In any case, long term studies of magnets as they apply to humans are needed. Another drawback of the existing systems with respect to a magnetic jewelry, is that the therapeutic response—if any—is limited and narrow with respect to the field of use.

Therefore, with respect to jewelries that may be utilized for the purpose of achieving a therapeutic effect, there is a need for an alternative to the copper bracelet and the magnetic jewelries that are found in the present market. Such alternative may require a mode of operation that is different from the modes of operation of the existing copper bracelet and magnetic jewelries. In this regard, an examination of alternative modes of operation for a passive therapeutic jewelry needs to be considered.

First, referring to eastern philosophies, and specifically the Indian belief of a human CHAKRA SYSTEM, a representation of what is referred to in eastern medicine and philosophy as the human Chakra system is described. According to eastern philosophy, the human Chakras are points in the body in which a vortex-like flow reversal occurs, establishing a strong energy point in the human body. Like acupuncture, the concept of a "Chakra" system in human beings has not been embraced by conventional western medicine. However, it is interesting to note that the Chakra points do coincide with acupuncture points. Furthermore, the Chakra point of the Heart (#4, Anahata/Anandakanda) has special relevance to the invention disclosed here.

Referring now to publicly available HUMAN ACUPUNCTURE CHARTS, a representation of various human acupuncture and acupressure points are described. Unlike the "Chakra" concept, acupuncture has had some acceptance in western medicine, although this acceptance has only happened over a period of decades. As may be seen in Acupuncture Charts, there is a strong Chi (energy) point at the same point as the #4 Chakra. This is known as the Shanzhong point, and is indicative of the primary energy flow point in the human body. For further clarification, this point is located on the anterior midline, at the level of the fourth intercostals space. An additional point of interest is the Zhongji point, located 4 cun below the umbilicus, and is indicative of the crossing point of the ren channel. This is not to say that there are not additional points of interest in the acupuncture system.

Referring now to the work of Davis and Rawls (Magnetism and its effect on the living system by Albert Roy Davis and Walter C. Rawls, April 1996, Acres USA Publications), a view has been illustrated for actual electrical measurements made on the front surfaces of a human body. These measurements were performed by Albert Roy Davis and Walter Rawls at the Albert Roy Davis Research Laboratory in Florida. The findings of these two researchers indicate that the right side of the human body is positively (electrically) charged and the left side of the human body is negatively charged. These findings also indicate the average voltages that were recorded at various locations of the human body. It is worth noting that the vicinity of the #4 Chakra point shows the highest voltage among all the points on the human body. This would also coincide with the belief in the acupuncture system that the Shanzhong point is the strongest Chi point in the human body.

Referring again to Rawls and Davis (Magnetism and its effect on the living system by Albert Roy Davis and Walter C. Rawls, April 1996, Acres USA Publications), a view has been illustrated for the electromagnetic equators of the human body. Of interest with respect to the invention disclosed here is the point in the center of the chest, which Davis and Rawls state that according to their findings, this point is where voltage change is noted, and at this point there is zero voltage when measuring from the crotch to this point. Again, this corresponds well with the Chakra system and the acupuncture system.

In addition, the body of evidence supporting acupuncture has reached the point of being irrefutable. This said, a conclusion may be reached that in addition to blood flowing through the human body, there is also an energy flow through the human body.

In order to understand the energy flow through the human body, a phenomenon of a thermomagnetic field may need to be considered. A thermomagnetic field may be obtained when a group of dissimilar metals is arranged so as to form a coil, with each dissimilar metal junction being alternately heated and cooled. To illustrate this effect, reference is now made to the work of Schroeder, with publicly titled documents (U.S. Pat. No. 5,393,350 and U.S. Pat. No. 5,597,976) entitled THERMOELECTRIC GENERATOR AND MAGNETIC ENERGY STORAGE UNIT invented by Schroeder. In operation, this device is capable of obtaining a low voltage, high current within the ring structure resulting in a magnetic field of 10 to 20 tesla. The magnetic field produced is so strong that the ring requires structural reinforcement with Kevlar or the like. The point made here is that this device produces a magnetic field in a novel manner, a method that does not use an electrical input but rather an input of heat.

Referring now to FIG. 1, a human body as illustrated relates to temperature differential. As illustrated in FIG. 1, human beings maintain a core temperature that is higher with respect to the extremities of the hands and feet. This differential is well known in the art and may be viewed in detail via infrared imaging techniques well known to those of skilled in the art. Due to this temperature differential as well as other factors, the conditions necessary for the production of thermomagnetic fields within the human body may be present. This phenomenon is scientifically plausible when one considers temperature differential, the presence of dissimilar metal components in the body such as Iron (blood) and Copper (collagen, enzymes, etc.), and the manner in which the blood flows via the circulatory system (flow reversals at extremities). In eastern philosophy, the thermomagnetic field is referred to as the "Aura", and is shown to extend several inches from the body. This would be consistent with magnetism. Furthermore, Kirlian photography technique records a field of energy emanating several inches from humans and plants, again consistent with magnetic fields.

If there is indeed a magnetic energy field that extends from the surface of a human body, then it should be possible to construct a passive apparatus that would be capable of interacting with this field, and altering the properties of this field. As an example, in acupuncture, a practitioner utilizes known techniques to detect "blockages" to energy flows in the human body. When the locations of these blockages are determined, then either needles or pressure is applied to this point for the purpose of relieving and removing the blockages. Accordingly, another drawback of the existing systems is a lack of an apparatus that can be placed over specific acupuncture points and that can interact with a humans' energy field and promote energy flow and circulation in a similar mode of operation to acupuncture but without needles or physical contact.

When considering the flow of either fluids or energy, we now consider vortex flows that consist of either centripetal or centrifugal forces, and how these flows might be produced passively. As will be recalled, a vortex may have an inward spiraling flow (centripetal) or an outward spiraling flow (centrifugal). In nature, the tornado is an example of a phenomena that illustrates both flow types. Further, it is often stated that an inward spiraling vortex is associated with a build-up of energy, such as the destructive tip of the tornado, while an outward spiraling vortex is associated with a dilution of energy.

Various chemical species in the human body and biochemical materials may also need to be considered since they may play a role in interacting with energy fields within the human body. To this end, Left-Handed and Right-Handed molecules may need to be considered. It is known that the Left-Handed group of molecules known as amino acids are utilized in the body for the purpose of building protein structures such as muscle tissue. This process of the amino acid forming a "building block" for a larger protein structure is generally recognized as being a solely chemical process. However, if all naturally occurring amino acids are considered Left-Handed (amino acids are isomers and demonstrate the phenomena of optical chirality), and that light passing through an amino acid will bend to the left, a thermomagnetic field in the presence of an L-amino acid would orient itself to the left as well. Accordingly, at the molecular level, in the process of the amino acid being used to form a protein, the human thermomagnetic field twists to the left in the presence of the L-amino acid, causing the thermomagnetic field to spin clockwise (inward) which creates a buildup of energy, with this energy assisting in the formation of the new protein structure.

Similarly, some sugars such as sucrose may play a role in the human body. Common table sugar is a right-handed molecule. Thus, the human thermomagnetic field in the presence of sugar would spin counter-clockwise thereby creating a centrifugal flow which would lead to the dissipation of an energy field. This would at first seem to be inconsistent with the role that sugar plays in the body, which would be to create the basic building blocks of energy units (ATP). However, if we examine the actual chemical process that sugar is involved in, then we know that in order for sugar to enter the ATP cycle, it must first be broken down. Accordingly, at the molecular level, in the process of the sugar being broken down so that it may be used for the creation of ATP, the human thermomagnetic field twists to the right in the presence of the sugar, causing the thermomagnetic field to spin counter-clockwise (outward) which creates a dissipation of the structure, with this energy assisting in the destruction of the sugar molecule.

If these effects are occurring within the human body, then it should be possible to create a device that passively interacts with the human body in such a way so as to promote the build-up or flow of energy within the human body.

Therefore, another drawback of the existing system is a lack of an apparatus and a method for regulating the energy-flow, thereby producing a beneficial response within the human body.

These and other drawbacks also exist.

SUMMARY OF THE INVENTION

The invention overcomes these and other drawbacks.

In one embodiment, the invention provides an apparatus that produces a beneficial effect when placed on a human body. In some embodiments, the beneficial effect may include, for example, strength increase, stamina increase, pain relief, etc.

In one embodiment, the invention provides an apparatus that regulates thermomagnetic energy flow within a human body.

In one embodiment, the invention provides an apparatus that produces a beneficial effect when placed on a human body, wherein the apparatus regulates thermodynamic energy-flow within the human body for producing the beneficial effect.

In one embodiment, the invention provides an apparatus that includes biomolecular components for regulating thermomagnetic energy flow within a human body. In one embodiment, the biomolecular components may include molecules associated with building-up of energy (e.g., thermomagnetic energy). In another embodiment, the biomolecular components may include molecules associated with dilution of energy (e.g., thermomagnetic energy). In yet another embodiment, the biomolecular components may include molecules associated with building-up of energy (e.g., thermomagnetic energy) and dilution of energy (e.g., thermomagnetic energy). In a further embodiment, the biomolecular components may include orthomolecular and/or non-orthomolecular organic materials capable of thermomagnetic levororotary action and/or thermomagnetic dextrorotatory action.

In one embodiment, the invention provides an apparatus including biomolecular components associated with building-up of energy, wherein the biomolecular components may include, for example, but not limited to a Left-Handed molecule such as an amino acid (e.g., L-Glutamine).

In one embodiment, the invention provides an apparatus including biomolecular components associated with dilution of energy, wherein the biomolecular components may include, for example, but not limited to a Right-Handed molecule such as sugar, D-Glutamic acid, etc.

In one embodiment, the invention provides an apparatus including one or more substrates, for example, but not limited to a polyester, cotton fabric sheet, etc., for biomolecular components that regulate thermomagnetic energy flow within a human body.

In one embodiment, the invention provides an apparatus including a sealed plastic enclosure, wherein the sealed plastic enclosure may enclose biomolecular components regulating thermomagnetic energy flow within a human body and one or more substrates for the biomolecular components.

In one embodiment, the invention provides an apparatus that includes a sealed plastic enclosure having biomolecular components regulating thermomagnetic energy flow within a human body and one or more substrates for the biomolecular components, wherein the apparatus further includes one or more gem stones (e.g., Jade, powdered jade, etc.) for decorative purpose.

In one embodiment, the invention provides one or more physical structural settings for holding components of an apparatus. In some embodiments, said one or more physical structural settings may hold biomolecular components regulating thermomagnetic energy flow within a human body, one or more substrates for said biomolecular components, and one or more gem stones (e.g., Jade, powdered jade, etc.) for decorative purpose.

In one embodiment, the invention provides an apparatus that produces a beneficial effect, for example improvement in strength/stamina, when placed on a human body, wherein the apparatus may comprise one or more of components including, for example, Left-Handed molecules (e.g., L-Glutamine), one or more substrates (e.g., a polyester, cotton fabric sheet, etc.) for said Left-Handed molecules, a sealed enclosure (e.g., plastic film enclosure) enclosing said Left-Handed molecules and said one or more substrates, one or more gem stones or similar materials (e.g., jade, etc.).

In one embodiment, the invention provides an apparatus that produces a beneficial effect, for example relief from a pain, when placed on a human body, wherein the apparatus may comprise one or more of components including, for example, Right-Handed molecules (e.g., sucrose, D-Glutamic acid, etc.), one or more substrates (e.g., a polyester, cotton fabric sheet, etc.) for said Right-Handed molecules, a sealed enclosure (e.g., plastic film enclosure) enclosing said Right-Handed molecules and said one or more substrates, one or more gem stones or similar materials (e.g., jade, etc.).

In one embodiment, the invention provides an apparatus that may be in one or more of a plurality of wearable objects such as dermal patches, bracelets, pendants, support pads, shirts, socks, foot inserts, etc.

In some embodiments, the invention provides a non-transdermal patch having Left-Handed molecules for improving strength/stamina for a user. According to the invention, the non-transdermal patch having Left-Handed molecules may be manufactured with the following specifications:

500 mg of L-Glutamine is added to 15 ml of distilled water; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the L-Glutamine solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

In other embodiments, the invention provides a non-transdermal patch having Right-Handed molecules for relieving from a pain for a user. According to the invention, the non-transdermal patch having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

In one embodiment, the invention provides a method for fabricating an apparatus that produces a beneficial effect when placed on a human body, wherein the apparatus regulates thermomagnetic energy-flow within the human body for producing the beneficial effect.

In one embodiment, the invention provides a method for placing an apparatus on a human body or into a human body, wherein the apparatus produces a beneficial effect when placed on the human body or into the human body, wherein the apparatus regulates thermomagnetic energy-flow within the human body for producing the beneficial effect.

Other objects and features of the invention will become apparent from the following detailed description considered in connection with the accompanying drawings that disclose embodiments of the invention. It should be understood, however, that the drawings are designed for purposes of illustration only and not as a definition of the limits of the invention.

BRIEF DESCRIPTIONS OF THE DRAWINGS

DETAILED DESCRIPTION OF THE INVENTION

Figure 1:
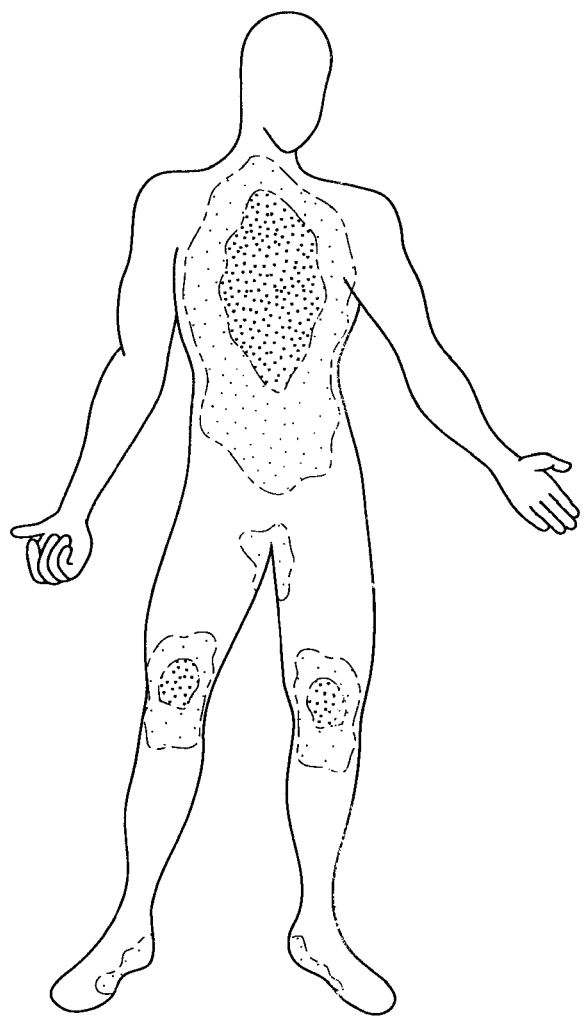
FIG. 1 illustrates temperature differential in a human body.

According to one embodiment, the invention provides an apparatus that produces a beneficial effect when placed on a human body, wherein the apparatus regulates thermodynamic energy-flow within the human body for producing the beneficial effect. In some embodiments, the beneficial effect may include, for example, strength increase, stamina increase, and pain relief.

According to another embodiment, the invention provides an apparatus that may include biomolecular components for regulating thermomagnetic energy flow within a human body. In one embodiment, the biomolecular components may include molecules associated with building-up of energy (e.g., thermomagnetic energy). In another embodiment, the biomolecular components may include molecules associated with dilution of energy (e.g., thermomagnetic energy). In yet another embodiment, the biomolecular components may include molecules associated with building-up of energy (e.g., thermomagnetic energy) and dilution of energy (e.g., thermomagnetic energy). In a further embodiment, the biomolecular components may include orthomolecular (e.g., naturally occurring organic compounds) and/or non-orthomolecular organic materials capable of thermomagnetic levororotary action and/or thermomagnetic dextrorotatory action.

According to another embodiment, the invention provides an apparatus that may include orthomolecular organic compounds (e.g., naturally occurring organic compounds) and or non-orthomolecular organic compounds for inducing one or more beneficial effects such as, for example, strength increase, stamina increase, pain relief, etc.

Some of the orthomolecular and non-orthomolecular organic compounds may be more fully described as complex organic structures with asymmetric carbon atoms capable of either thermomagnetic levorotatory action due to the proton pulling forces associated with thermomagnetic fields or thermomagnetic dextrorotatory action due to the proton pulling forces associated with thermomagnetic fields. In both cases, according to one embodiment of the invention, the orthomolecular and/or nonorthomolecular organic materials utilized may be arranged parallel with respect to the plane of thermomagnetic rotation.

According to another embodiment, the invention provides an apparatus, wherein the apparatus functions on the basis of the principle that the proton pulling forces associated with human thermomagnetic fields are capable of interacting with passive orthomolecular and or non-orthomolecular organic materials so long as these materials are arranged parallel to the plane of rotation, with this arrangement inducing electron flow due to well known and long established electromotive principles.

It is known that hemoglobin is an Iron-containing pigment of red blood cells. Its function is to carry Oxygen from the lungs to other tissues. It is also known that collagen is a Copper containing, fibrous insoluble protein in connective tissues, including skin, bone, ligaments and cartilage. In addition, human beings possess a natural temperature differential from the core to the extremities.

In physics, the Seebeck effect describes a phenomena in which when an apparatus consists of two metals (such as Iron and Copper), with one metal at a higher temperature than the other, a current flows in the apparatus. The Thomson thermoelectric effect is the designation of the potential gradient along a conductor which accompanies a temperature gradient.

The thermomagnetic phenomena arises in that the thermoelectric and thermomagnetic power is measured by electromotive force produced by the unit difference of temperature, in this case the temperature differential from the core to the extremities. In short, all of the conditions necessary for human beings to produce thermomagnetic fields are present in humans.

According to another embodiment, the invention provides a passive apparatus that includes orthomolecular and non-orthomolecular organic compounds for improving one or more beneficial effects (e.g., strength, stamina, human performance, etc.) by interacting with a human thermomagnetic field. This interaction may induce an increased electron flow within a human body. In some embodiments, this interaction is not unlike the effect that occurs in an electrical generator in which electricity is produced from moving magnets or magnetic fields.

In humans, an increase in electron flow has numerous demonstrable benefits with one being an immediate and measurable increase in physical strength. This is not a chemically induced increase, in strength such as would be the case with anabolic steroids, etc., but rather a phenomena in which existing muscle mass is utilized more efficiently due to the increase in electron flow.

To understand how this phenomena could be possible, if we examine the striated skeletal muscle apparatus we know that this voluntary group nerve supply is under conscious control because these nerves are branches of the peripheral cerebrospinal nervous apparatus (the brain and spinal cord as the cerebrospinal axis), The muscle fibers themselves are tissues composed of contractile cells that effect movement based on the excitatory process set up in nerve fibers by stimuli (the nerve impulse). It is presently believed by medical research that the nerve impulse is probably in the nature of a wave of electrochemical disturbances. The efficiency with which the nerve impulse controls a specific muscle group can be defined as the number of muscle fibers utilized in a contraction divided by the number of fibers present in that muscle group. It is presently believed that most humans only contract a small percentage of muscle fibers in a given group for a given nerve impulse (low efficiency of muscle mass usage per nerve impulse contraction).

If now we were to induce a condition in which the total power of the electrochemical nerve impulse could be increased so that more muscle fibers could contract for a given nerve impulse, the net efficiency of the striated fibers would increase (more muscle fibers in a group being contracted for a nerve impulse), and hence usable physical strength could be improved. This is one possible explanation for the phenomena associated with beneficial effects, for example, immediate and demonstrable increases in strength and stamina within seconds of wearing the wearable apparatus of the present invention.

This phenomena is not unusual or unknown in other devices. For example, in physical therapy electrical signals are utilized for the purpose of forcing voluntary muscle groups to contract under stimulation. These devices are commonly known as electrical or electronic muscle stimulators (EMS) and cause stimulated contraction and relaxation phases of muscle groups. According to another embodiment, the invention provides an apparatus for, based on the mode of operation as presented, an improvement in net efficiency of total muscle mass utilized during a contraction phase that may be achieved due to an increase in electron flow during the wave of electrochemical disturbances created by the nerve impulse.

According to another aspect, the invention provides an apparatus that passively modulates the oscillating low energy magnetic field that exists just above the surface of the human epidermal layer. This passive frequency modulation creates a condition in which the transport of long chain fatty acids across the mitochondrial membrane for subsequent beta-oxidation and energy production is triggered or improved, thereby providing a user of the apparatus with increased energy via an increase in ATP production as described above.

To understand this phenomenon, the metabolic process involving fatty acid energy sources within the human body can be examined. Fatty acids, a hydrocarbon in which one of the hydrogen atoms has been replaced by a carboxyl group, are also described as a monobasic aliphatic acid made up of an alkyl radical attached to a carboxyl group. The metabolic role of fatty acids may be described in part in that fatty acids are one of the primary sources of energy for humans and, through Beta-Oxidation, are broken down into basic units of energy. Of interest here is that, in order for this process to work, fatty acids need to enter the mitochondria for Beta-Oxidation, and they are unable to penetrate the inner mitochondrial membrane by themselves. In the human body, to overcome the problem of the inability of fatty acids to transport from the cytosol (soluble portion of the cell) across the mitochondrial membrane, it has been determined by several researchers that various nutrients are essential to transport long chain fatty acids from the cytosol across the mitochondrial membrane for fatty acid oxidation/metabolism and energy production.

According to the invention, in order to obtain the desirable effect of improving cell metabolism passively (specifically, increasing the rate of fatty acid Beta-Oxidation by allowing fatty acids to transport across the mitochondrial membrane), an apparatus consisting of orthomolecular organic structures can be designed to passively interact with the human magnetic field for the purpose of creating a system of frequency modulation, much in the same way that radio waves are modulated to communicate audio information.

According to an embodiment of the invention, an apparatus 100 that causes a beneficial effect by regulating thermomagnetic energy-flow within a human body are illustrated in FIGS. 2A, 2B, 3A, and 3B.

According to another embodiment, the invention provides apparatus 100 comprising biomolecular components that may include molecules associated with building-up of energy (e.g., thermomagnetic energy). In some embodiments, biomolecular components may include a Left-Handed molecule such as, for example, an amino acid. In one embodiment, the apparatus may include a structure that may be used for promoting the flow of energy (electrons) within a human body so as to improve physical strength of a user, wherein the structure may include a Left-Handed molecule such as, for example, an amino acid.

The Left-Handed amino acids are known in those skilled in the art, and as such a complete description of the Left-Handed amino acids need not be given here, but suffice it to say that suitable Left-Handed amino acids for use in the invention may include, for example, L-Glutamine, L-Arginine, L-Ornithine, L-Carnitine, L-Taurine, L-Tryptophan, L-Glycine, etc. Preferably, the amino acids used in the invention are orthomolecular amino acids.

In some embodiments, the Left-Handed molecule is an amino acid found in nature. In other embodiments, the Left Handed molecule is an amino acid synthesized by man. The examples of amino acids may include, but not limited to, L-Alanine, L-Arginine, L-Aspargine, L-Aspartic Acid, L-Carnitine, Acetyl-L-Carnitine, L-Carnitine L-Tartrate, L-Carnitine Magnesium Citrate, L-Citrulline, L-Cystine, L-Cystine, L-GABA, L-Glutamic Acid, L-Glutamine, Glutathione Peroxidase, L-Glycine, L-Histidine, Hydroxyglutamic Acid, Hydroxyproline, L-Isoleucine, L-Leucine, Norleucine, L-Lysine, LMethionine, L-Ornithine, L-Valine, L-Phenylalanine, L-Proline, L-Serine, L-Taurine, L-Threonine, L-Tryptophan, L-Tyrosine, etc. In some embodiments, the Left-Handed molecules may include a synthetic L-sugar (L-glucose) or other synthetic levo-rotatory molecule known to one skilled in the art.

According to another embodiment of the invention, the Left-Handed molecule may be employed in a variety of ways. In one example, the biomolecular components including the Left-Handed molecules may be used in the form of a liquid, with said liquid being sprayed or similarly applied to a substrate. In another example, the biomolecular components including the Left-Handed molecule may be used in the form of a solid, such as a powder, with said powder being mixed with a binder such as latex rubber, silicone rubber, epoxy, wax or the like, with the powdered amino acid and binder being applied to a substrate.

According to another embodiment, the invention may include a structure that includes a plurality of Left-Handed molecules. In other words, more than one kind of Left-Handed molecules may be utilized in a structure. In one example, a structure in which L-glutamine may be applied to a single substrate, followed by the layering of a second amino acid such as L-Arginine to a second substrate, with both treated substrates forming part of the completed structure of the invention. In some embodiments, portions of L-Glutamine and L-Arginine may be mixed together, and then applied in the form of a liquid or powder to a single substrate. In another example, two or more L amino acids may be applied to the same substrate.

According to another embodiment, the invention provides an apparatus comprising biomolecular components that may include molecules associated with dilution of energy (e.g., thermomagnetic energy). In some embodiments, the biomolecular components may include Right-Handed molecules such as, for example, an amino acid. In one embodiment, the apparatus may include a structure that may be used for negating flow of energy (electrons) within a human body so as to decrease physical strength of a user or relax the user, wherein the structure may include Right-Handed molecules such as, for example, an amino acid or sugar.

The Right-Handed amino acids and Right-Handed sugars are known to those skilled in the art, and as such a complete description of these materials need not be given here, but suffice it to say that suitable Right-Handed amino acids (i.e., D amino acids) for use in the present invention may include, for example, D-Glutamine, D-Arginine, D-Ornithine, D-Carnitine, D-Taurine, D-Tryptophan, D-Glycine, D-Glutamic Acid, etc.

In some embodiments, the Right-Handed molecule is an amino acid found in nature. In other embodiments, the Right-Handed molecule is an amino acid synthesized by man. The Examples of the Right-Handed molecule may include, but not limited to, D-Alanine, D-Arginine, D-Aspargine, D-Aspartic Acid, D-Carnitine, Acetyl-D-Carnitine, D-Carnitine D-Tartrate, D-Carnitine Magnesium Citrate, D-Citrulline, D-Cysteine, D-Cystine, D-GABA, D-Glutamic Acid, D-Glutamine, D-Glutathione Peroxidase, D-Glycine, D-Histidine, D-Hydroxyglutamic Acid, D-Hydroxyproline, D-Soleucine, D-Leucine, D-Norleucine, D-Lysine, D-Metbionine, D-Ornithine, D-Valine, D-Phenylalanine, D-Proline, D-Serine, D-Taurine, D-Threonine, D-Tryptophan, D-Tyrosine, etc.

According to another embodiment, the Right-Handed molecules may include one or more sugars, for example, but not limited to dextrin, dextrose, fructose, galactose, glucose, glycogen, high fructose corn syrup, honey, inositol, invert sugar, lactose, levulose, maltose, molasses, sucrose, sugar cane, and xylose etc. Preferably, the Right-Handed amino acids used in the invention are non-orthomolecular amino acids.

According to another embodiment of the invention, the Right-Handed molecules may be employed in a variety of ways. In one example, the biomolecular components including the Right-Handed molecules may be used in the form of a liquid, with said liquid being sprayed or similarly applied to a substrate. In another example, biomolecular components including the Right-Handed molecules may be used in the form of a solid, such as a powder, with said powder being mixed with a binder such as latex rubber, silicone rubber, epoxy, wax or the like, with the powdered amino acid and binder being applied to a substrate.

According to another embodiment, the invention may include a structure that includes a plurality of Right-Handed molecules. In other words, more than one kind of Right-Handed molecules may be used in a structure. In one example, a structure in which D-Glutamic acid may be applied to a single substrate, followed by the layering of a second D amino acid to a second substrate, with both treated substrates forming part of the completed structure of the invention. In some embodiments, portions of D-Glutamic acid and a second D amino acid may be mixed together, and then applied in the form of a liquid or powder to a single substrate. In another example, two or more D amino acids may be applied to the same substrate.

According to another embodiment, the invention provides an apparatus including one or more substrates for the biomolecular components regulating thermomagnetic energy flow within a human body. In some embodiments, the one or more substrates may include, for example, but not limited to a polyester fabric sheet, a cotton fabric sheet, etc. In one embodiment, the one or more substrates may be used for the Left-Handed molecules. In another embodiment, the one or more substrates may be used for the Right Handed molecules. The one or more substrates may not react (chemically, etc.) with the Left-Handed molecules and the Right-Handed molecules of the invention. The examples of substrates may include, for example, but not limited to polyester fabric sheet (e.g., manufactured by Pellon, #910, an interfacing material for lightweight to featherweight fabrics, etc.), cotton fabric sheet, etc. In one embodiment, either the polyester fabric sheet or the cotton fabric sheet may be used in construction of the apparatus of the invention. In another embodiment, both the polyester fabric sheet and the cotton fabric sheet may be used in construction of apparatus 100 of the invention.

According to another embodiment, the invention may include one or more additives for the Left-Handed molecules and/or Right-Handed molecules. The examples of additives may include, but not limited to Glycerin, d-calcium pantothenate, sorbitol, propylparaben, potassium sorbate, methylparaben, Colloidal Gold, etc.

According to another embodiment, the invention provides an apparatus including a sealed enclosure, wherein the sealed enclosure may enclose biomolecular components (e.g., Left-Handed molecules, Right-Handed molecules) regulating thermomagnetic energy flow within the human body and one or more substrates for the biomolecular components. The sealed enclosure may be made of a material, for example, but not limited to a polyester film sheet (e.g., manufactured by GBC, a thermal laminating film, etc.), a plastic film (e.g., polyethylene, polypropylene, ABS, plexiglass, lexan, pvc, etc), etc. In one embodiment, the polyester film sheet and/or the plastic film may be utilized in construction of the apparatus of the invention. In some embodiments the sealed enclosure may be made of a light polarizing film. In other embodiments the sealed enclosure may be made of a linear low density film.

According to another embodiment of the invention, the sealed enclosure may not react (i.e., chemically, etc.) with biomolecular components (e.g., Left-Handed molecules, Right-Handed molecules) of the invention. In some embodiments, the sealed enclosure may be capable of being sealed in a predefined fashion to keep the Left-Handed molecules and/or the Right-Handed molecules in a liquid state. In some embodiments, the sealed enclosure may be capable of being sealed in a predefined fashion to protect the Left-Handed molecules and/or the Right-Handed molecules from ambient environmental conditions.

Methods of sealing plastic films are known to those skilled in the art and will not be described here in detail. Examples of such methods of sealing plastic films may include, for example, pressure sensitive or thermally sensitive adhesives, ultrasonic sealing, etc.

According to another embodiment, the invention provides an apparatus that includes a sealed plastic enclosure that encloses biomolecular components regulating thermomagnetic energy flow within the human body and one or more substrates for the biomolecular components, wherein the apparatus further includes one or more gem stones (e.g., Jade, powdered jade, etc.).

In one embodiment, Jade may be used for decorative purposes, and for the practice of the invention. Jade (or other gem stones) may be incorporated into the invention in either gem stone form, or in powdered form. If Jade is incorporated in stone form, then the apparatus of the invention may be embodied as decorative items such as jewelry, etc. If Jade is incorporated in powdered form, then the Jade powder may be added to the Left-Handed molecules and/or the Right-Handed molecules. The Jade may also be added in other parts of the devices of the invention so as to make the apparatus practical for use.

According to another embodiment, the invention provides one or more physical structural settings for holding one or more components of apparatus 100. In some embodiments, that the one or more physical structural settings may hold biomolecular components regulating thermomagnetic energy flow within the human body, one or more substrates for the biomolecular components, and one or more gem stones (e.g., Jade, powdered jade, etc.).

According to another embodiment, apparatus 100 may be in one or more of a plurality of wearable objects, for example, but not limited to dermal patches, bracelets, pendants, support pads, shirts, socks, foot inserts, etc.

According to another embodiment, the invention may include a patch having an adhesive (e.g., medical grade adhesive). In some embodiments, the invention may include a single patch. In other embodiments, the invention may include a plurality of patches. In one embodiment, the patch may be constructed in layers made of plastic film or light polarizing film, polyester fabric as a substrate, Water, L-Carnitine, Glycerin, d-calcium pantothenate, sorbitol, propylparaben, potassium sorbate, and methylparaben. In another embodiment, the patch may be constructed in layers made of a plastic film or a light polarizing film as an enclosure, a polyester fabric as a substrate, Honey and Molasses.

If apparatus 100 of the present invention is embodied as jewelry items, then the apparatus may be mounted in virtually any jewelry setting that is already commercially available, provided that the setting does not interfere in any way with the operation of apparatus 100 of the present invention. If apparatus 100 of the invention is embodied in "Band Aid" style or "Transdermal Patch" style, then a setting would not be needed. In one embodiment, apparatus 100 of the invention may be completely sealed, thereby the Left-Handed molecules and/or the Right-Handed molecules may not make direct contact with a user of apparatus 100. In addition, the Left-Handed molecules and/or the Right-Handed molecules may not enter into body of the user.

In some embodiments, Apparatus 100 of the invention having Left-Handed molecules may be manufactured with the following specifications:

500 mg of L-Glutamine is added to 15 ml of distilled water; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the L-Glutamine solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

In other embodiments, Apparatus 100 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

According to another embodiment, the invention provides a method for placing apparatus 100 on a predetermined location of a human body or into a human body, wherein apparatus 100 produces a beneficial effect when placed on the human body or into the human body, wherein apparatus 100 regulates thermodynamic energy-flow within the human body for producing the beneficial effect. The apparatus 100 may include, for example, patch, bracelet, necklace, anklet, etc.

According to another embodiment, the invention provides methods for placing apparatus 100 of the invention into proximity of a human body. In one example, apparatus 100 of the invention may be attached to pendants, and allowed to be placed into proximity of the human body. In another example, apparatus 100 of the invention may be embodied in "Band Aid" style or "Patch" style, with a medical grade adhesive being applied to the device to make it suitable for use with human beings.

In one embodiment, apparatus 100 (e.g., dermal patch) may be placed on forearms of a user for producing a beneficial effect such as, for example, improvement in strength or stamina. In some embodiments, apparatus 100 (e.g., dermal patch) having Left-Handed molecules may be placed on the palm side of the right forearm of the user. In other embodiments, apparatus 100 (e.g., dermal patch) having Right-Handed molecules may be placed on the palm side of the left forearm of the user.

For strength and stamina, apparatus 100 (e.g., dermal patch) may be placed at Pericardium 4 (P4) located about 4 inches below the wrist.

For relief of sinus congestion, apparatus 100 (e.g., dermal patch) may be placed on Large Intestine 14 (LI 14). In some embodiments, apparatus 100 (e.g., dermal patch) having Left-Handed molecules may be placed on RIGHT shoulder and apparatus 100 (e.g., dermal patch) having Right-Handed molecules may be placed on left shoulder for relief of sinus congestion.

For relief of menstrual cramps, woman may place apparatus 100 (e.g., dermal patch) having Left-Handed molecules at the depression on the midline of the chest and apparatus 100 (e.g., dermal patch) having Right-Handed molecules at about 1-2 inches below the belly button (where the cramps are).

For relief of knee pain from arthritis, apparatus 100 (e.g., dermal patch) having Left-Handed molecules may be placed along the midline at the depression between the chest and apparatus 100 (e.g., dermal patch) having Right-Handed molecules may be placed where the pain is on the knee.

In a preferred embodiment, apparatus 100 (e.g., dermal patch) having Left-Handed molecules may be placed at an electrically POSITIVE point on the body and apparatus 100 (e.g., dermal patch) having Right-Handed molecules may be placed at an electrically NEGATIVE point on the body. Positive and Negative points on the body have been metered and been well known by physiologists for about 3o years+.

Furthermore, apparatus 100 (e.g., dermal patch) may be placed at known acupuncture points. For example, apparatus 100 having Left-Handed molecules (e.g., POSITIVE dermal patch) may be placed at a YANG (positive) point and apparatus 100 (e.g., dermal patch) having Right-Handed molecules (e.g., NEGATIVE dermal patch) may be placed at a TIN (negative) point.

Figure 2A:
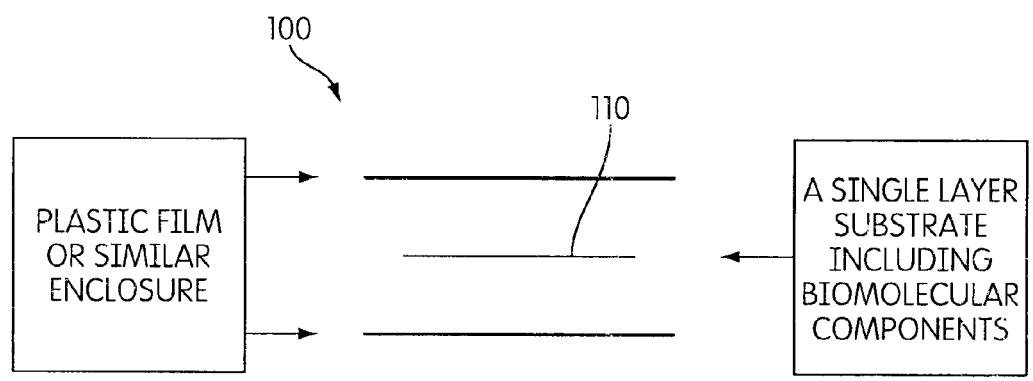
FIG. 2A illustrates an example of an apparatus including a single layer fabric substrate for retaining biomolecular components, according to an embodiment of the invention.

According to another embodiment of the invention illustrated in FIG. 2A, apparatus 100 that causes a beneficial effect (e.g., improvement in strength/stamina, relief from a pain, etc.) by regulating thermomagnetic energy flow within a human body may include a single layer fabric substrate 110 for retaining biomolecular components including, for example, molecules for building-up of energy (e.g., thermomagnetic energy) and/or molecules for dilution of energy (e.g., thermomagnetic energy). Apparatus 100, as illustrated, may be fabricated in accordance with the principles as described here in the preceding disclosure.

Figure 2B:
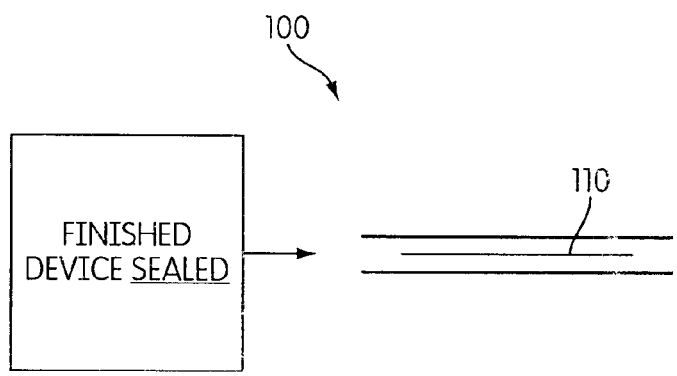
FIG. 2B illustrates an example of a sealed apparatus including a single layer fabric substrate for retaining biomolecular components, according to an embodiment of the invention.

FIG. 2B illustrates a sealed single layer fabric substrate that retain the biomolecular components.

Figure 3A:
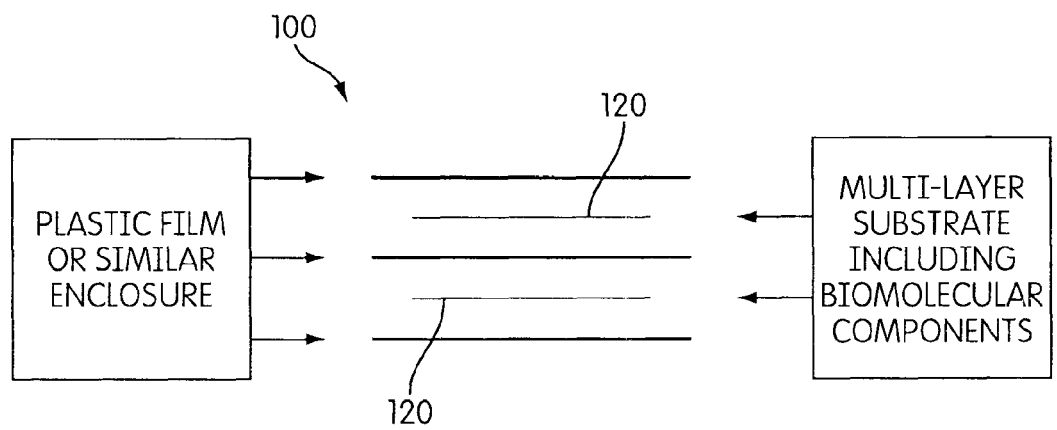
FIG. 3A illustrates an example of an apparatus including a multi-layer fabric substrate for retaining biomolecular components, according to an embodiment of the invention.

According to another embodiment of the invention illustrated in FIG. 3A, apparatus 100 that causes a beneficial effect (e.g., improvement in strength/stamina, relief from a pain, etc.) by regulating thermomagnetic energy-flow within a human body may include two layers of fabric substrate 120 for retaining biomolecular components including, for example, molecules for building-up of energy (e.g., thermomagnetic energy) and/or molecules for dilution of energy (e.g., thermomagnetic energy). Apparatus 100, as illustrated, may be fabricated in accordance with the principles as described here in the preceding disclosure.

Figure 3B:
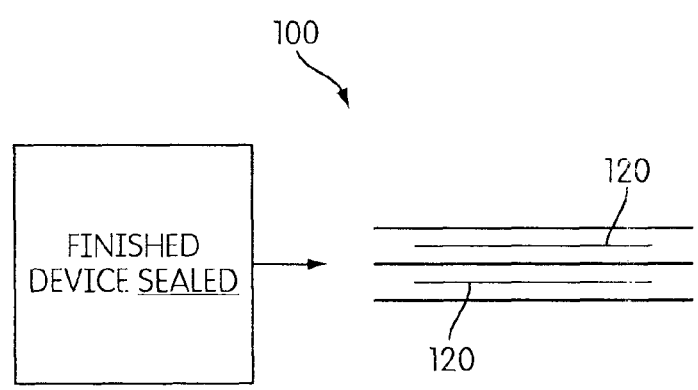
FIG. 3B illustrates an example of a sealed apparatus including a multi-layer fabric substrate for retaining biomolecular components, according to an embodiment of the invention.

FIG. 3B illustrates a sealed multi layer fabric substrate that retain the biomolecular components.

Figure 4:
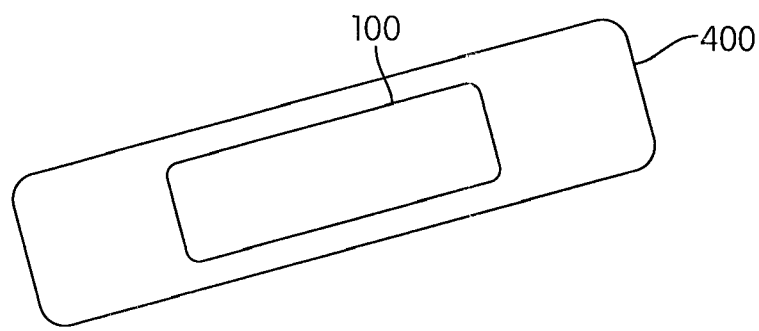
FIG. 4 illustrates an example of a patch including a biomolecular apparatus that causes a beneficial effect within a human body, according to an embodiment of the invention.

According to another embodiment of the invention illustrated in FIG. 4, a patch 400 may include apparatus 100 for causing a beneficial effect (e.g., improvement in strength/stamina, relief from a pain, etc.) for a human body by regulating thermomagnetic energy flow within the human body. In some embodiments, one or more portions of patch 400 may include medical grade adhesive for enabling attachment of patch 400 to human skin surface.

Figure 5:
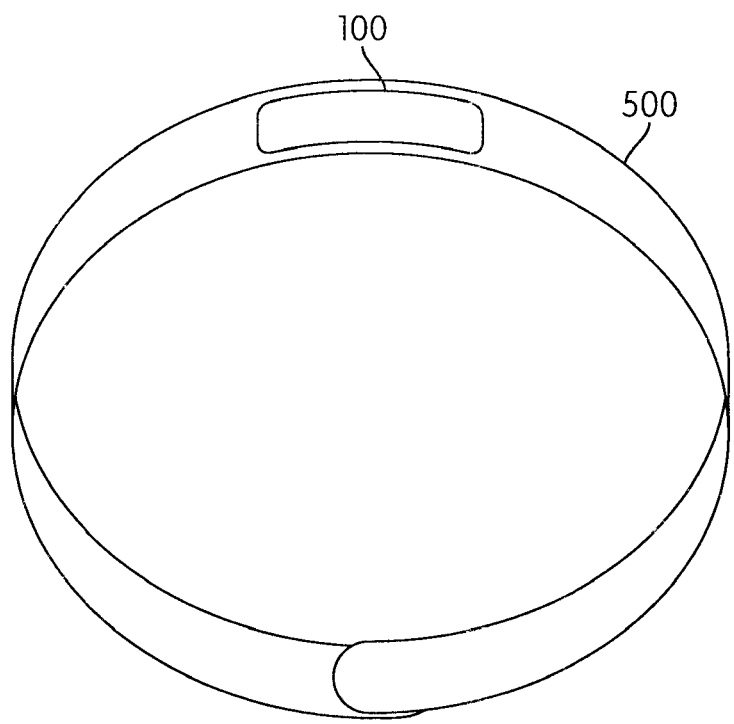
FIG. 5 illustrates an example of a bracelet including a biomolecular apparatus that causes a beneficial effect within a human body, according to an embodiment of the invention.

According to another embodiment of the invention illustrated in FIG. 5, a bracelet 500 may include apparatus 100 for causing a beneficial effect (e.g., improvement in strength/stamina, relief from a pain, etc.) for a human body by regulating thermomagnetic energy flow within the human body. In some embodiments, bracelet 500 may also include a gem stone (not shown in FIG. 5).

Figure 6:
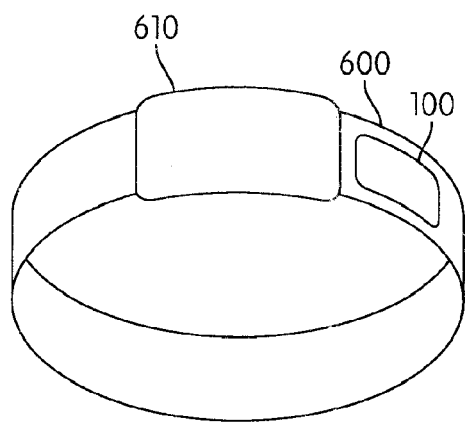
FIG. 6 illustrates an example of a ring including a biomolecular apparatus that causes a beneficial effect within a human body, according to an embodiment of the invention.

According to another embodiment of the invention illustrated in FIG. 6, a ring 600 may include apparatus 100 for causing a beneficial effect (e.g., improvement in strength/stamina, relief from a pain, etc.) for a human body by regulating thermomagnetic energy flow within the human body. In some embodiments, ring 600 may also include a gem stone 610.

Figure 7:
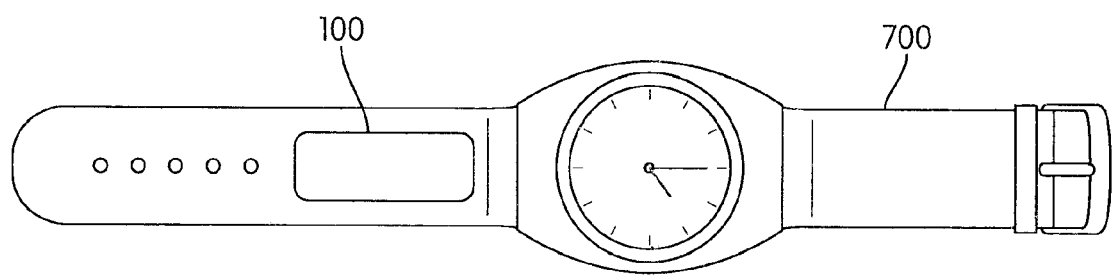
FIG. 7 illustrates an example of a watch including a biomolecular apparatus that causes a beneficial effect within a human body, according to an embodiment of the invention.

According to another embodiment of the invention illustrated in FIG. 7, a watch 700 may include apparatus 100 for causing a beneficial effect (e.g., improvement in strength/stamina, relief from a pain, etc.) for a human body by regulating thermomagnetic energy flow within the human body.

EXAMPLES

Example 1

Patch 400 of the invention having Left-Handed molecules may be manufactured with the following specifications:

500 mg of L-Carnitine is added to 15 ml of distilled water; A Pellon 100% polyester interfacing material is cut to a 1" diameter disk; GBC Heat Laminating films (#3000038 clear polyester substrate with homopolymer adhesive) are cut to 1.69" in diameter. The interfacing material is dipped in the L-Carnitine solution so as to saturate the fabric with the solution. The saturated fabric disk is then sandwiched and placed between 2 layers of the heat laminating film, and the structure is sealed with a heating surface so as to form the completed structure.

Patch 400 of the invention having Right-Handed molecules may be manufactured with the following specifications:

Honey in its raw form (Sioux Honey) is utilized as the patch ingredient. A Pellon 100% polyester interfacing material is cut to a 1" diameter disk; GBC Heat Laminating films (#3000038 clear polyester substrate with homopolymer adhesive) are cut to 1.69" in diameter. The interfacing material is dipped in the Honey so as to saturate the fabric with the solution. The honey-saturated fabric disk is then sandwiched and placed between 2 layers of the heat laminating film, and the structure is sealed with a heating surface so as to form the completed structure.

The above patches were tested with users by placing patch 400 having Left-Handed molecules on the right arms and patch 400 having Right-Handed molecules on the left arms; it was found that when using a hand dynamometer there was an average 15% increase in hand strength when using these patches as opposed to not using them. In other tests it was found that strength endurance (stamina) was increased over 20% on average when using this formulation as opposed to not using these patches.

Example 2

Patch 400 of the invention having Left-Handed molecules may be manufactured with the following specifications:

500 mg of L-Carnitine is added to 15 ml of distilled water; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the L-Carnitine solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right arms and patch 400 having Right-Handed molecules on the left arms; it was found that when using a hand dynamometer there was an average 15% increase in hand strength when using these patches as opposed to not using them. In other tests it was found that strength endurance (stamina) was increased over 20% on average when using this formulation as opposed to not using these patches. This formulation was utilized in the Morehouse College Clinical Study and the Troy State University Clinical Study.

Example 3

Patch 400 of the invention having Left-Handed molecules may be manufactured with the following specifications:

500 mg of L-Glutamine is added to 15 ml of distilled water; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the L-Glutamine solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right arms and patch 400 having Right-Handed molecules on the left arms; it was found that when using a hand dynamometer there was an average 10% increase in hand strength when using these patches as opposed to not using them. In other tests it was found that strength endurance (stamina) was increased over 15% on average when using this formulation as opposed to not using these patches.

Example 4

Patch 400 of the invention having Left-Handed molecules may be manufactured with the following specifications:

500 mg of L-Carnitine is added to 15 ml of distilled water; To this solution small amounts of preservatives are added so as to prevent the formation of mold or bacteria. In this case the preservatives that are added are glycerin, potassium sorbate, methylparaben and propylparaben. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the L-Glutamine solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredients. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right arms and patch 400 having Right-Handed molecules on the left arms; it was found that when using a hand dynamometer there was an average 15% increase in hand strength when using these patches as opposed to not using them. In other tests it was found that strength endurance (stamina) was increased over 20% on average when using this formulation as opposed to not using these patches.

Example 5

Patch 400 of the invention having Left-Handed molecules may be manufactured with the following specifications:

500 mg of L-Glutamine is added to 15 ml of distilled water; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the L-Glutamine solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right arms and patch 400 having Right-Handed molecules on the left arms; it was found that when using a hand dynamometer there was an average 10% increase in hand strength when using these patches as opposed to not using them. In other tests it was found that strength endurance (stamina) was increased over 15% on average when using this formulation as opposed to not using these patches.

Example 6

Patch 400 of the invention having Left-Handed molecules may be manufactured with the following specifications:

500 mg of acetyl-L-Carnitine is added to 15 ml of glycerin; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the acetyl-1-carnitine solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right arms and patch 400 having Right-Handed molecules on the left arms; it was found that when using a hand dynamometer there was an average 15% increase in hand strength when using these patches as opposed to not using them. In other tests it was found that strength endurance (stamina) was increased over 25% on average when using this formulation as opposed to not using these patches.

Example 7

Patch 400 of the invention having Left-Handed molecules may be manufactured with the following specifications:

500 mg of acetyl-l-carnitine and 100 mg of L-Ornithine are added to 30 ml of glycerin; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the amino acid solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right arms and patch 400 having Right-Handed molecules on the left arms; it was found that when using a hand dynamometer there was an average 15% increase in hand strength when using these patches as opposed to not using them. In other tests it was found that strength endurance (stamina) was increased over 25% on average when using this formulation as opposed to not using these patches.

Example 8

Patch 400 of the invention having Left-Handed molecules may be manufactured with the following specifications:

500 mg of acetyl-1-carnitine and 100 mg of L-Arginine are added to 30 ml of glycerin; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the amino acid solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right arms and patch 400 having Right-Handed molecules on the left arms; it was found that when using a hand dynamometer there was an average 15% increase in hand strength when using these patches as opposed to not using them. In other tests it was found that strength endurance (stamina) was increased over 25% on average when using this formulation as opposed to not using these patches.

Example 9

Patch 400 of the invention having Left-Handed molecules may be manufactured with the following specifications:

500 mg of L-Arginine is added to 15 ml of distilled water; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the L-Arginine solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right arms and patch 400 having Right-Handed molecules on the left arms; it was found that when using a hand dynamometer there was an average 10% increase in hand strength when using these patches as opposed to not using them. In other tests it was found that strength endurance (stamina) was increased over 20% on average when using this formulation as opposed to not using these patches.

Example 10

Patch 400 of the invention having Left-Handed molecules may be manufactured with the following specifications:

500 mg of L-Ornithine is added to 15 ml of distilled water; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the L-Ornithine solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right arms and patch 400 having Right-Handed molecules on the left arms; it was found that when using a hand dynamometer there was an average 10% increase in hand strength when using these patches as opposed to not using them. In other tests it was found that strength endurance (stamina) was increased over 20% on average when using this formulation as opposed to not using these patches.

Example 11

Patch 400 of the invention having Left-Handed molecules may be manufactured with the following specifications:

500 mg of L-Glutamic Acid is added to 15 ml of distilled water; A Pellon 100% polyester interfacing material is cut to a 1" diameter disk; GBC Heat Laminating films (#3000038 clear polyester substrate with homopolymer adhesive) are cut to. 1.69" in diameter. Two pieces of the interfacing material are dipped in the L-Glutamic Acid solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right arms and patch 400 having Right-Handed molecules on the left arms; it was found that when using a hand dynamometer there was an average 10% increase in hand strength when using these patches as opposed to not using them. In other tests it was found that strength endurance (stamina) was increased over 15% on average when using this formulation as opposed to not using these patches.

Example 12

Patch 400 of the invention having Left-Handed molecules may be manufactured with the following specifications:

500 mg of L-Glycine is added to 15 ml of distilled water; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the L-Glycine solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right arms and patch 400 having Right-Handed molecules on the left arms; it was found that when using a hand dynamometer there was an average 10% increase in hand strength when using these patches as opposed to not using them. In other tests it was found that strength endurance (stamina) was increased over 15% on average when using this formulation as opposed to not using these patches.

Example 13

Patch 400 of the invention having Left-Handed molecules may be manufactured with the following specifications:

150 mg of L-Isoleucine, 150 mg of L-Leucine and 150 mg of L-Valine are added to 30 ml of distilled water; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the amino acid solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right anus and patch 400 having Right-Handed molecules on the left arms; it was found that when using a hand dynamometer there was an average 10% increase in hand strength when using these patches as opposed to not using them. In other tests it was found that strength endurance (stamina) was increased over 25% on average when using this formulation as opposed to not using these patches.

Example 14

Patch 400 of the invention having Left-Handed molecules may be manufactured with the following specifications:

500 mg of L-Methionine is added to 15 ml of distilled water; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the L-Methionine solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right arms and patch 400 having Right-Handed molecules on the left aims; it was found that when using a hand dynamometer there was an average 10% increase in hand strength when using these patches as opposed to not using them. In other tests it was found that strength endurance (stamina) was increased over 20% on average when using this formulation as opposed to not using these patches.

Example 15

Patch 400 of the invention having Left-Handed molecules may be manufactured with the following specifications:

500 mg of L-Taurine is added to 15 ml of distilled water; A Pellon 100% polyester interfacing material is cut to a 1" diameter disk; GBC Heat Laminating films (#3000038 clear polyester substrate with homopolymer adhesive) are cut to 1.69" in diameter. Two pieces of the interfacing material are dipped in the L-Taurine solution so as to saturate the fabrics with the solution. The saturated fabric disks are then sandwiched and placed between separate layers of the heat laminating film (the saturated disks are separated from one another by plastic films), and the structure is sealed with a heating surface so as to form the completed structure.

Patch 400 of the invention having Right-Handed molecules may be manufactured with the following specifications:

Honey in its raw form (Sioux Honey) and unsulphured Molasses (Grandma Molasses) is utilized as the patch ingredient. The ratio of Honey to Molasses is 3 lb. of honey by weight to 355 ml of Molasses. A Pellon 100% polyester interfacing material is cut to a I" diameter disk; GBC Heat Laminating films (#3000038 clear polyester substrate with homopolymer adhesive) are cut to 1.69" in diameter. Two pieces of the interfacing material are dipped in the Honey/Molasses solution so as to saturate the fabric with the solution. The honey/molasses-saturated fabric disks are then sandwiched and placed between layers of the heat laminating film (the saturated disks are separated from one another by plastic films), and the structure is sealed with a heating surface so as to form the completed structure.

The above patches were tested with users by placing patch 400 having Left-Handed molecules on the right arms and patch 400 having Right-Handed molecules on the left arms; it was found that when using a hand dynamometer there was an average 10% increase in hand strength when using these patches as opposed to not using them. In other tests it was found that strength endurance (stamina) was increased over 20% on average when using this formulation as opposed to not using these patches.

Example 16

The invention provides a new supplement and method for the improvement of athletic performance, and more particularly a means by which an individual may increase their net stamina/strength endurance output. To quantitatively assess the effectiveness of the invention in improving the bench press performance of fatigued college football athletes during team training, a double-blind placebo controlled study was implemented at Morehouse College in Atlanta, Ga., with 44 college athletes from the school's football team volunteering to participate in this study. In most evaluations of strength endurance involving competitive athletes, it is common and customary to perform both baseline and comparative tests prior to the athlete having performed any other type of physical activity. In this study, both baseline and comparative data were collected after the athletes had been fatigued by a 60-minute heavy weight-training workout. In addition, it was also decided to test the athletes while under heavy physical trauma. The athletes performed the workout and tests starting at 4:30 a.m. in a weight training room where the temperature was maintained in excess of 95° F. The standardized exercise that was chosen for this test was a 185 pound or 225 pound bench press.

Using a double-blind randomized placebo controlled study, a total of 44 subjects, ages 18 to 30 years, volunteered to participate for this study. Subjects' baseline bench press data was collected after a normal prescribed off-season football upper body 60-minute workout session. Subjects were asked to bench press a fixed weight until failure.

In the next session, subjects were randomized into three groups using a numbering system that labeled participants as experiment group, placebo group or control group members with 44 completing this two-session study. The placebo group was provided with dermal patches that had placebo water formula. The experimental group was provided with experimental dermal patches. The experimental dermal patches included either patch 400 having Left-Handed molecules or patch 400 having Right-Handed molecules or both. In the experimental group, patch 400 having left-handed molecules was placed on the palm side of the right forearm of the participants, and patch 400 having right-handed molecules was placed on palm side of the left forearm of the participants. In the placebo group, placebo dermal patches were placed on palm sides of both the left arm and the right arm of the participants. A collection team independent of the players collected and monitored data throughout the study process.

Data collected from the two-day study was as follows. All numbers listed are repetitions performed:

mance of 3.1% from the baseline tests to the comparative tests; (2) the average percentage change in strength endurance in the Placebo group was an increase in performance of 3.6% from the baseline tests to the comparative tests; (3) the average percentage change in strength endurance in the Experiment group was an increase in performance of 33.9% from the baseline tests to the comparative tests.

In addition, the data shows the following:

| CONTROL GROUP | | | PLACEBO GROUP | | | EXPERIMENT GROUP | | |
|---|---|---|---|---|---|---|---|---|
| Decrease | Same | Increase | Decrease | Same | Increase | Decrease | Same | Increase |
| 5 | 6 | 5 | 4 | 2 | 7 | 3 | 2 | 10 |

In the Control group, applicants found that 31.25% of the participants showed a decrease in performance during the two-day study, 37.5% of the participants maintained the same level of performance during the two-day study, and 31.25% of the participants showed an increase in performance during the two-day study. In the Placebo group, applicants found that 30.8% of the participants showed a decrease in performance during the two-day study, 15.4% of the participants maintained the same level of performance during the two-day study, and 53.8% of the participants showed an increase in performance during the two-day study. In the Experiment group, applicants found that 20% of the participants showed a decrease in performance during the two-day study, 13.33% of the participants maintained the same level of performance during the two-day study, and 66.67% of the participants showed an increase in performance during the two-day study.

After removing the data for the individuals who both decreased in performance and maintenance the same level of performance, applicants found that (1) in the Control group, with respect to the 5 individuals who did show an improvement in performance from the baseline to the comparative test, the average increase in strength endurance was 24.4%; (2) in the Placebo group, with respect to the 7 individuals who did show an improvement in performance from the baseline to the comparative test, the average increase in strength endurance was 23%; (3) in the Experimental group, with

| CONTROL GROUP | | | PLACEBO GROUP | | | EXPERIMENT GROUP | | |
|---|---|---|---|---|---|---|---|---|
| Baseline | Comparative | % Change | Baseline | Comparative | % Change | Baseline | Comparative | % Change |
| 6 | 4 | −33 | 8 | 8 | 0 | 12 | 10 | −17 |
| 10 | 12 | 20 | 7 | 8 | 14 | 1 | 3 | 200 |
| 9 | 11 | 22 | 5 | 6 | 20 | 6 | 12 | 100 |
| 5 | 5 | 0 | 4 | 3 | −25 | 4 | 6 | 50 |
| 12 | 12 | 0 | 6 | 3 | −50 | 2 | 3 | 50 |
| 10 | 10 | 0 | 15 | 18 | 20 | 5 | 3 | −40 |
| 10 | 9 | −10 | 12 | 10 | −17 | 9 | 9 | 0 |
| 2 | 3 | 50 | 11 | 13 | 18 | 11 | 15 | 36 |
| 3 | 0 | −100 | 12 | 12 | 0 | 3 | 4 | 33 |
| 4 | 4 | 0 | 7 | 10 | 43 | 18 | 16 | −11 |
| 10 | 12 | 20 | 16 | 21 | 31 | 15 | 16 | 7 |
| 5 | 4 | −20 | 20 | 23 | 15 | 6 | 9 | 50 |
| 10 | 9 | −10 | 9 | 7 | −22 | 16 | 16 | 0 |
| 5 | 5 | 0 | | | | 4 | 5 | 25 |
| 15 | 15 | 0 | | | | 8 | 10 | 25 |
| 10 | 11 | 10 | | | | | | |

From the data collected in the above table, it was determined that (1) the average percentage change in strength endurance in the Control group was a decrease in perfor- respect to the 10 individuals who did show an improvement in performance from the baseline to the comparative test, the average increase in strength endurance was 57.6%.

After removing the data for the individuals who both increased in performance and maintained the same level of performance, applicants found that (1) in the Control group, with respect to the 5 individuals who decreased in performance from the baseline to the comparative test, the average decrease in strength endurance was 34.6%; (2) in the Placebo group, with respect to the 4 individuals who decreased in performance from the baseline to the comparative test, the average decrease in strength endurance was 28.5%; (3) in the Experiment group, with respect to the 3 individuals who decreased in performance from the baseline to the comparative test, the average decrease in strength endurance was 22.67%.

Based on the data collected, it is evident that there are several distinct differences in athletic performance between the three test groups. With respect to the simple averaging of performance numbers, it is not unusual that the Control group experienced a decrease in strength endurance given the nature of the test (baseline data collected on a Monday and comparative data collected on a Thursday; data collected after athletes were fatigued). With respect to the Placebo group, a case could be made that there was indeed a "Placebo effect" that took place; athletes that wore the patch product thought that they had the real technology so, hence, they made more of an effort to perform. Given the data of the average group performance improvement of 3.6%, this would be a reasonable spread in terms of attainable improvements from the baseline day to the comparative day. With respect to the Experiment group, a case could be made that there was indeed a significant effect of the experimental dermal patch on athletic performance; athletes that wore the patch product experienced an average improvement of 33.9% in strength performance. The spreads in average performance numbers between the three groups is significant and would tend to indicate that the experimental dermal patch played an important role in improving strength endurance in the experiment group.

Another indicator that the experimental dermal patch was having a significant effect on athletic stamina is evidenced in the chart. As could be expected, in the Control group, there is an almost even distribution between athletes that decreased in performance, athletes that remained the same in performance, and athletes that improved in performance. In the Placebo group, 7 individuals improved in performance as compared to 5 in the Control group. However, given the low average improvement in members and the well-known "Placebo effect," this spread is anticipated. In the Experiment group, only 3 members decreased in performance, with 10 members improving in strength endurance. Given that the Experiment group had the highest percentage of members who recorded an improvement in performance, with two-thirds of the members demonstrating an improvement, and that the average improvement was significantly higher than the other two groups (33.9%), this would again indicate that the experimental dermal patch was having a beneficial effect on athletic performance. Another potentially important indicator with respect to examining whether or not the experimental dermal patch was having a beneficial effect on athletic performance is found when looking at only those individuals who increased in performance or only those individuals who decreased in performance. In the Control group, applicants found that of those individuals how did show an improvement, the average gain was 24.4%; of those in the Control group who decreased in performance, the average decline in performance was 34.6%. In the Placebo group, applicants found that of those individuals who did show an improvement, the average gain was similar to the Control group at 23%; of those in the Placebo group who decreased in performance, applicants found that the average decline in performance was 28.5%. In the Experiment group, applicants found that of those individuals who did show an improvement, the average gain was more than double of the other two groups at 57.6%; of the three individuals who showed a decrease in performance, the average decline in performance was the lowest of the three groups at 22.67%. This information clearly indicates that the experimental dermal patch was having a beneficial effect on strength endurance.

Based on the data collected and the results obtained, it was demonstrated that the invention (i.e., experimental dermal patch) provides a method for the improvement of athletic performance, and more particularly a means by which an individual may increase their net stamina/strength endurance output. It was also demonstrated that the Experiment group using the invention (i.e., experimental dermal patch showed the highest percentage of improvement in strength endurance when averaging all members, the highest percentage of improvement in strength endurance when averaging only those members who showed an improvement, and the lowest percentage of decreased performance when averaging only those individuals who showed a decline in performance.

Example 17

The invention provides a new supplement and method for the improvement of athletic performance, and more particularly a means by which individuals may substantially increase their net strength endurance within as quickly as the first use of the product. To quantitatively assess the effectiveness of the invention in improving the bench press performance of college football athletes during team training, a double-blind placebo controlled study was implemented at Troy State University in Troy, Ala. A standardized test was selected to measure net gains in strength endurance, and in this case the exercise that was performed by all athletes was a 225 pound flat bench, press. The baseline data for this test was collected on Thursday Jun. 26, 2003. The comparative data was collected on the following Wednesday Jul. 2, 2003. Athletes were divided into three groups: Control, Placebo and Test. The Control group was tested "as is" on both of these testing days. The Placebo group was given a set of patches filled with water; this group was unaware as to whether or not the patches were real or water filled. The Test group was given a set of patches of the invention; again, this group was unaware as to the contents of the patches. It should be emphasized that the athletes used the patches of the invention only once; the test was performed within 10 minutes of first applying the patches to the athletes.

Using a double-blind randomized placebo controlled study, a total of 25 subjects, ages 18 to 22 years, volunteered to participate for this test study. Subjects' baseline bench press data was collected after a brief warm up period. Subjects were asked to bench press a fixed 225 pound weight until failure. In the next session, subjects were randomized into three groups using a numbering system that labeled participants as Test group, Placebo group or Control group members with 25 completing this two-session study. The Test group was provided with non-transdermal patches that included either patch 400 having Left-Handed molecules or patch 400 having Right-Handed molecules or both. In the test group, patch 400 having left-handed molecules was placed on the palm side of the right forearm of the participants, and patch 400 having right-handed molecules was placed on palm side of the left forearm of the participants. The Placebo group was provided with non-transdermal patches that contained water. In the placebo group, placebo dermal patches were placed on palm sides of both the left arm and the right arm of the participants. A collection team independent of the players collected and monitored data throughout the study process.

Data collected from the two-day study was as follows; all numbers listed are repetitions performed:

| CONTROL | | | | PLACEBO | | | | TEST | | | |
|---|---|---|---|---|---|---|---|---|---|---|---|
| Baseline | Comparative | ˆReps | ˆPercent | Baseline | Comparative | ˆReps | ˆPercent | Baseline | Comparative | ˆReps | ˆPercent |
| 10 | 10 | 0 | 0 | 23 | 23 | 0 | 0 | 3 | 8 | +5 | +166.7% |
| 4 | 6 | +2 | +50% | 10 | 10 | 0 | 0 | 16 | 15 | −1 | −6.2% |
| 12 | 14 | +2 | +16.7% | 7 | 12 | +5 | +71.4% | 8 | 9 | +1 | +12.5% |
| 9 | 10 | +1 | +11.1% | 21 | 24 | +3 | +14.3% | 16 | 18 | +2 | +12.5% |
| 10 | 13 | +3 | +30% | 14 | 8 | −6 | −42.8% | 7 | 15 | +8 | +114.3% |
| 5 | 6 | +1 | +20% | 10 | 11 | +1 | +10% | 5 | 8 | +3 | +60% |
| 20 | 21 | +1 | +4.7% | 26 | 27 | +1 | +3.8% | 12 | 14 | +2 | +16.7% |
| 18 | 19 | +1 | +5.5% | 11 | 17 | +6 | +54.5% | | | | |
| 6 | 5 | −1 | −16.7% | | | | | | | | |
| 18 | 11 | −7 | −38.9% | | | | | | | | |

From the data collected in the above table, and by removing the highest and lowest scores from each group, it was determined that (1) the average percentage change in strength endurance in the Control group was an increase in performance of 8.9% from the baseline tests to the comparative tests (average 0.875 rep improvement); (2) the average percentage change in strength endurance in the Placebo group was an increase in performance of 13.8% from the baseline tests to the comparative tests (average 1.67 rep improvement); and (3) the average percentage change in strength endurance in the Test group was an increase in performance of 43.2% from the baseline tests to the comparative tests (average 2.6 rep improvement).

In addition, the data shows the following:

| CONTROL GROUP | | | PLACEBO GROUP | | | TEST GROUP | | |
|---|---|---|---|---|---|---|---|---|
| Decrease | Same | Increase | Decrease | Same | Increase | Decrease | Same | Increase |
| 2 | 1 | 7 | 1 | 2 | 5 | 1 | 0 | 6 |

The above table provides the breakdown of athletes in each group as it pertains to showing whether or not an athlete showed a decrease in performance from baseline to comparative test, remained the same in performance from baseline to comparative test, or showed an increase in performance from baseline to comparative test.

In the Control group, Applicants found that 20% of the participants showed a decrease in performance during the two-day study, 10% of the participants maintained the same level of performance during the two-day study, and 70% of the participants showed an increase in performance during the two-day study. In the Placebo group, Applicants found that 12.5% of the participants showed a decrease in performance during the two-day study, 25% of the participants maintained the same level of performance during the two-day study, and 62.5% of the participants showed an increase in performance during the two-day study. In the Test group, Applicants found that 14.3% of the participants showed a decrease in performance during the two-day study, 0% of the participants maintained the same level of performance during the two-day study, and 85.7% of the participants showed an increase in performance during the two-day study.

After removing the data for the individuals who both decreased in performance and maintained the same level of performance, Applicants found that (1) in the Control group, with respect to the 7 individuals who did show an improvement in performance from the baseline to the comparative test, the average increase in strength endurance was 19.7%; (2) in the Placebo group, with respect to the 5 individuals who did show an improvement in performance from the baseline to the comparative test, the average increase in strength endurance was 30.8%; (3) in the Test group, with respect to the 6 individuals who did show an improvement in performance from the baseline to the comparative test, the average increase in strength endurance was 63.8%.

After removing the data for the individuals who both increased in performance and maintained the same level of performance, Applicants found that (1) in the Control group, with respect to the 2 individuals who decreased in performance from the baseline to the comparative test, the average decrease in strength endurance was 27.8%; (2) in the Placebo group, with respect to the 1 individual who decreased in performance from the baseline to the comparative test, the decrease in strength endurance was 42.8%; (3) in the Experiment group, with respect to the 1 individual who decreased in performance from the baseline to the comparative test, the decrease in strength endurance was 6.2%.

Based on the data collected, it is evident that there are several distinct differences in athletic performance between the three groups. With respect to the simple averaging of performance numbers, it is not unusual that all three groups experienced an increase in strength endurance given the nature of the test (athletes were in a training session for the upcoming football season). With respect to the Placebo group, a case could be made that there was indeed a "Placebo Effect" that took place; athletes that wore the patch product thought that they had the real technology so hence they made more of an effort to perform. Given the data of the average group performance improvement of the Placebo group of 13.8% (as compared to 8.9% in the Control group), this would be a reasonable spread in terms of attainable improvements from the baseline day to the comparative day. With respect to the Test group, there was indeed a significant effect of the test dermal patch on athletic performance; athletes that wore the pitch product experienced an average improvement of 43.2% in strength performance. The spreads in average performance numbers between the three groups is significant and would tend to indicate that the test dermal patch played an important role in improving strength endurance in the test group.

Another indicator that the test dermal patch was having a significant effect on athletic stamina is evidenced in the Table. In all three groups, Applicants found that the majority of the athletes improved in performance; however, the Control group and Placebo group showed nearly identical percentages of athletes that improved, with 70% of the Control group and 62.5% of the Placebo group. By comparison in the Test group, Applicants found that 85.7% of the participants experienced an improvement in performance. Given that the Test group had the highest percentage of members who recorded an improvement in performance, with 85.7% of the members demonstrating an improvement, and that the average improvement was significantly higher than the other two groups (43.2%) this would again indicate that the test dermal patch was having a beneficial effect on athletic performance.

Another important indicator with respect to examining that the test dermal patch was having a beneficial effect on athletic performance is found when looking at only those individuals who increased in performance or only those individuals who decreased in performance. In the Control group, Applicants found that, of those individuals who did show an improvement, the average gain was 19.7%. In the Placebo group, Applicants found that, of those individuals who did show an improvement, the average gain was close to the Control group at 30.8%. In the Test group, Applicants found that, of those individuals who did show an improvement, the average gain was more than triple the Control group and double the Placebo group at 63.8%. This information would indicate that the test dermal patch was having a beneficial effect on strength endurance. This improvement is dramatic in that the individuals tested had only used the test dermal patch for 10 minutes prior to the test.

Based on the data collected and the results obtained it was demonstrated that the invention (i.e., test dermal patch) provides a method for the improvement of athletic performance, and more particularly a means by which an individual may increase their net stamina/strength endurance output. The model utilized to evaluate the technology was a double-blind placebo controlled study, with 25 college athletes from the Troy State University football team volunteering to participate in this study. In this evaluation of strength endurance involving competitive athletes both baseline and comparative tests were performed prior to any other type of physical activity.

It was demonstrated that the group using the invention (i.e., test dermal patch) showed the highest percentage of improvement in strength endurance when averaging all members, the highest percentage of improvement in strength endurance when averaging only those members who showed an improvement, and the lowest percentage of decreased performance when averaging only those individuals who showed a decline in performance.

While a particular embodiment of the present invention has been described, it is to be understood that modifications will be apparent to those skilled in the art without departing from the spirit of the invention. The scope of the invention, therefore, is to be determined solely by the following claims.

What is claimed is:

1. A system for application to a subject's body to provide a beneficial biological effect for the subject selected from an increase in muscular strength and an increase in strength endurance, the system comprising at least one Left-Handed organic material-containing apparatus and at least one Right-Handed organic material-containing apparatus for application to a subject's body:
   A. the at least one Left-Handed organic material-containing apparatus for application to a first position on a subject's body comprises
      1 at least one organic material including a Left-Handed molecule selected from the group consisting of L-Carnitine, L-Glutamine, acetyl-L-Carnitine, L-Ornithine, L-Arginine, L-Glutamic acid, L-Glycine, L-Leucine, L-Isoleucine, L-Valine, L-Methionine, L-Taurine, and mixtures thereof;
      2 at least one substrate for said at least one organic material; and
      3 at least one enclosure for said at least one organic material and said at least one substrate; and
   B. the at least one Right-Handed organic material-containing apparatus for application to a second position on a subject's body separate and distinct from the first position comprises
      1 at least one organic material including a Right-Handed molecule selected from honey, molasses, or combinations thereof;
      2 at least one substrate for said at least one organic material; and
      3 at least one enclosure for said at least one organic material and said at least one substrate,
   wherein the at least one Left-Handed organic material-containing apparatus and the at least one Right-Handed organic material-containing apparatus together provide the beneficial biological effect,
   wherein the first position is selected from the group consisting of the right arm, the right shoulder, the depression on the midline of the chest, an electrically positive point, and combinations thereof of the subject's body, and the second position is selected from the left arm, the left shoulder, about 1-2 inches below the belly button, the knee, an electrically negative point, and combinations thereof of the subject's body; and
   wherein the at least one enclosure for both the at least one Left-Handed organic material-containing apparatus and the at least one Right-Handed organic material-containing apparatus comprises an adhesive for adhering the at least one enclosure to said subject's body and wherein the at least one enclosure is comprised of one or more materials that prevent the at least one organic material from direct contact with the subject's body while the at least one enclosure is adhered to the subject's body using the adhesive.

2. The system of claim 1, wherein the combination of the Left-Handed organic material-containing apparatus and the Right-Handed organic material-containing apparatus is capable of causing the beneficial biological effect by interacting with a thermomagnetic energy-flow within the human body.

3. The system of claim 1, wherein the Left-Handed molecule is an amino acid, wherein said amino acid is selected from the group consisting of L-Arginine, L-carnitine, Acetyl-L-Carnitine, L-Methionine, L-Ornithine, and L-Taurine.

4. The system of claim 1, wherein the Left-Handed molecule is an amino acid, wherein said amino acid is selected from L-Carnitine, and Acetyl-L-Carnitine.

5. The system of claim 1, wherein the at least one substrate in the Left-Handed organic molecule-containing apparatus and/or the at least one substrate in the Right-Handed organic molecule-containing apparatus is polyester or cotton.

6. The system of claim 1, wherein said at least one enclosure in the Left-Handed organic molecule-containing apparatus and/or the at least one enclosure in the Right-Handed organic molecule-containing apparatus is made of a plastic film, wherein the plastic film is selected from the group consisting of polyethylene, polypropylene, ABS, plexiglass, lexan, light polarizing film, and linear low density film.

7. The system of claim 1, wherein the in the Left-Handed organic molecule-containing apparatus and/or the Right-Handed organic molecule-containing apparatus further comprises one or more adhesive portions so as to attach said apparatus on a skin surface of the subject.

8. The system of claim 7, wherein said one or more adhesive portions includes a medical grade adhesive.

9. The system of claim 1, wherein the first position is an electrically positive point on the body, and wherein the second position is an electrically negative point on the body.

10. The system of claim 1, wherein the Left-Handed organic molecule-containing apparatus and/or the Right-Handed organic molecule-containing apparatus further comprises one or more additives for said at least one organic material, wherein said one or more additives are selected from the group consisting of Glycerin, d-calcium pantothenate, sorbitol, propylparaben, potassium sorbate, methylparaben, and Colloidal Gold.

11. The system of claim 1, wherein said Left-Handed organic molecule-containing apparatus is a patch constructed in layers, said layers including a plastic film or a light polarizing film as an enclosure, a polyester fabric as a substrate, Water, L-Carnitine, Glycerin, d-calcium pantothenate, sorbitol, propylparaben, potassium sorbate, and methylparaben, and wherein said Right-Handed organic molecule-containing apparatus is a patch constructed in layers, said layers including a plastic film or a light polarizing film as an enclosure, a polyester fabric as a substrate, honey, and molasses.

* * * * *